(12) United States Patent
Fraser (10) Patent No.: US 10,543,503 B1
(45) Date of Patent: Jan. 28, 2020

(54) METHODS OF DELIVERY OF ENCAPSULATED PERFLUOROCARBON TAGGANTS

(71) Applicant: Copilot Ventures Fund III LLC, Wilmington, DE (US)

(72) Inventor: Jay Fraser, San Antonio, TX (US)

(73) Assignee: CoPilot Ventures Fund III LLC, Wilmington, DE (US)

( * ) Notice: Subject to any disclaimer, the term of this patent is extended or adjusted under 35 U.S.C. 154(b) by 260 days.

(21) Appl. No.: 15/477,675

(22) Filed: Apr. 3, 2017

Related U.S. Application Data (63) Continuation of application No. 14/740,149, filed on Jun. 15, 2015, now Pat. No. 9,610,597, which is a continuation of application No. 13/659,995, filed on Oct. 25, 2012, now Pat. No. 9,057,712.

(60) Provisional application No. 61/552,428, filed on Oct. 27, 2011.

(51) Int. Cl.
| | |
|---|---|
| B05B 17/06 | (2006.01) |
| B05B 1/30 | (2006.01) |
| B05B 9/04 | (2006.01) |
| G01N 21/64 | (2006.01) |

(52) U.S. Cl.
CPC ........... B05B 17/0607 (2013.01); B05B 1/30 (2013.01); B05B 9/0403 (2013.01); *G01N 21/6428* (2013.01); *G01N 2021/6439* (2013.01)

(58) Field of Classification Search
USPC ...................................................... 73/61.59
See application file for complete search history.

(56) References Cited

U.S. PATENT DOCUMENTS

| | | | |
|---|---|---|---|
| 3,991,680 A | * | 11/1976 | Dietz ..................... F42B 3/103 |
| | | | 102/275.9 |
| 4,256,038 A | | 3/1981 | Dietz et al. |
| 4,520,109 A | | 5/1985 | Simmonds et al. |
| 4,944,921 A | | 7/1990 | Colby et al. |
| 4,987,767 A | | 1/1991 | Corrigan et al. |
| 5,109,691 A | | 5/1992 | Corrigan et al. |
| 5,173,298 A | | 12/1992 | Meadows |
| 5,225,900 A | | 7/1993 | Wright |
| 5,301,044 A | | 4/1994 | Wright |
| 5,345,809 A | | 9/1994 | Corrigan et al. |
| 5,362,568 A | | 11/1994 | Dietz et al. |
| 5,409,839 A | * | 4/1995 | Balestrieri ............. D21H 21/46 |
| | | | 436/27 |
| 5,437,272 A | | 8/1995 | Fuhrman |

(Continued)

*Primary Examiner* — Natalie Huls
*Assistant Examiner* — Mohammed E Keramet-Amircolai
(74) *Attorney, Agent, or Firm* — Tully Rinckey PLLC; Steven M. Hoffberg (57) ABSTRACT

A system and method for tagging, tracking, locating and identifying people and vehicles transporting people using Perfluorocarbon tracers. An on-going problem faced by military as well as law enforcement personnel is that of friendly fire incidents. To prevent possible friendly-fire incidents, troops would separate the two layers of the uniform patch, thereby releasing a controlled release of the Perfluorocarbon vapors. Other "friendly" troops, equipped with sensors tuned to the specific perfluorocarbon characteristics would thus be able to literally view a plume around the tagged person or object. The system may conversely be used to tag enemies. Formulations of mixed perfluorocarbons may be used to provide coding of emissions.

21 Claims, 6 Drawing Sheets

Taggant Capsules on Substrate with Barrier Layer

Ruptures Capsules

(56) References Cited

U.S. PATENT DOCUMENTS

| | | | |
|---|---|---|---|
| 5,451,505 A | 9/1995 | Dollinger | |
| 5,465,607 A | 11/1995 | Corrigan et al. | |
| 5,543,177 A | 8/1996 | Morrison et al. | |
| 5,562,099 A | 10/1996 | Cohen et al. | |
| 5,581,257 A | 12/1996 | Greene et al. | |
| 5,585,112 A | 12/1996 | Unger et al. | |
| 5,585,575 A | 12/1996 | Corrigan et al. | |
| 5,600,303 A | 2/1997 | Husseiny et al. | |
| 5,692,029 A | 11/1997 | Husseiny et al. | |
| 5,751,629 A | 5/1998 | Nova et al. | |
| 5,853,752 A | 12/1998 | Unger et al. | |
| 5,859,362 A | 1/1999 | Neudorfl et al. | |
| 5,874,214 A | 2/1999 | Nova et al. | |
| 5,925,562 A | 7/1999 | Nova et al. | |
| 5,961,923 A | 10/1999 | Nova et al. | |
| 5,993,298 A | 11/1999 | Duescher | |
| 6,017,496 A | 1/2000 | Nova et al. | |
| 6,025,129 A | 2/2000 | Nova et al. | |
| 6,025,200 A * | 2/2000 | Kaish | G01N 21/643 422/83 |
| 6,071,495 A | 6/2000 | Unger et al. | |
| 6,100,026 A | 8/2000 | Nova et al. | |
| 6,196,056 B1 | 3/2001 | Ewing et al. | |
| 6,214,624 B1 | 4/2001 | Barker et al. | |
| 6,284,459 B1 | 9/2001 | Nova et al. | |
| 6,319,668 B1 | 11/2001 | Nova et al. | |
| 6,329,139 B1 | 12/2001 | Nova et al. | |
| 6,331,273 B1 | 12/2001 | Nova et al. | |
| 6,340,588 B1 | 1/2002 | Nova et al. | |
| 6,352,854 B1 | 3/2002 | Nova et al. | |
| 6,372,428 B1 | 4/2002 | Nova et al. | |
| 6,416,714 B1 | 7/2002 | Nova et al. | |
| 6,477,227 B1 | 11/2002 | Kaiser et al. | |
| 6,501,825 B2 | 12/2002 | Kaiser et al. | |
| 6,524,859 B1 | 2/2003 | Heese et al. | |
| 6,531,262 B1 | 3/2003 | Lawandy et al. | |
| 6,560,544 B1 | 5/2003 | Ondrus | |
| 6,566,645 B1 | 5/2003 | Murphey | |
| 6,572,784 B1 | 6/2003 | Coombs et al. | |
| 6,617,591 B1 | 9/2003 | Simonson et al. | |
| 6,659,175 B2 | 12/2003 | Malone et al. | |
| 6,780,564 B2 | 8/2004 | Lawandy et al. | |
| 6,850,592 B2 | 2/2005 | Schramm et al. | |
| 6,879,398 B2 | 4/2005 | Townsend et al. | |
| 6,881,381 B1 | 4/2005 | Asher et al. | |
| 6,908,737 B2 | 6/2005 | Ravkin et al. | |
| 6,909,770 B2 | 6/2005 | Schramm et al. | |
| 6,981,947 B2 | 1/2006 | Melker | |
| 7,032,662 B2 | 4/2006 | Malone et al. | |
| 7,038,766 B2 | 5/2006 | Kems et al. | |
| 7,052,468 B2 | 5/2006 | Melker et al. | |
| 7,052,854 B2 | 5/2006 | Melker et al. | |
| 7,060,992 B1 | 6/2006 | Barney | |
| 7,104,963 B2 | 9/2006 | Melker et al. | |
| 7,108,190 B2 | 9/2006 | Burgan et al. | |
| 7,112,445 B1 | 9/2006 | Welle | |
| 7,160,735 B2 | 1/2007 | Dehlinger et al. | |
| 7,211,240 B2 | 5/2007 | Arbogast et al. | |
| 7,253,435 B2 | 8/2007 | Siniaguine et al. | |
| 7,261,876 B2 | 8/2007 | Arbogast et al. | |
| 7,276,905 B2 | 10/2007 | Tamaroff et al. | |
| 7,279,073 B2 | 10/2007 | Bowman et al. | |
| 7,299,710 B2 | 11/2007 | Syage | |
| 7,304,300 B2 | 12/2007 | Partin et al. | |
| 7,410,011 B2 | 8/2008 | Anderson | |
| 7,488,451 B2 * | 2/2009 | Zarowitz | B01L 3/021 422/504 |
| 7,557,070 B2 | 7/2009 | Ravkin et al. | |
| 7,566,363 B2 | 7/2009 | Starling et al. | |
| 7,641,809 B2 | 1/2010 | Leck et al. | |
| 7,666,979 B2 | 2/2010 | Fan et al. | |
| 7,710,269 B2 | 5/2010 | Reep | |
| 7,718,578 B2 | 5/2010 | Griffiths et al. | |
| 7,720,254 B2 | 5/2010 | Stierman et al. | |
| 7,723,440 B2 | 5/2010 | Hogan et al. | |
| 7,727,775 B2 | 6/2010 | Willson et al. | |
| 7,742,170 B1 | 6/2010 | McNeil et al. | |
| 7,749,693 B2 | 7/2010 | Brassil et al. | |
| 7,767,457 B2 | 8/2010 | Mun et al. | |
| 7,807,344 B2 | 10/2010 | Dodd | |
| 7,820,009 B2 | 10/2010 | Gray et al. | |
| 7,820,108 B2 | 10/2010 | Lampotang et al. | |
| 7,829,162 B2 | 11/2010 | Eskra et al. | |
| 7,831,042 B2 | 11/2010 | Stierman et al. | |
| 7,854,919 B2 | 12/2010 | Arbogast et al. | |
| 7,885,428 B2 | 2/2011 | Stierman et al. | |
| 7,910,088 B2 | 3/2011 | Arbogast et al. | |
| 7,912,653 B1 | 3/2011 | Scher et al. | |
| 7,914,460 B2 | 3/2011 | Melker et al. | |
| 7,917,298 B1 | 3/2011 | Scher et al. | |
| 7,935,659 B2 | 5/2011 | Nova et al. | |
| 7,985,590 B2 | 7/2011 | McNeil | |
| 8,029,212 B2 | 10/2011 | Valerino, Sr. | |
| 8,033,450 B2 | 10/2011 | Stierman et al. | |
| 8,047,053 B2 | 11/2011 | Call et al. | |
| 8,053,744 B2 | 11/2011 | Bortolin | |
| 8,093,435 B2 | 1/2012 | Chiba et al. | |
| 8,124,414 B2 | 2/2012 | Harrup et al. | |
| 8,153,435 B1 * | 4/2012 | Fraser | G01N 33/0004 436/56 |
| 8,154,769 B2 | 4/2012 | McFarland et al. | |
| 8,158,433 B2 | 4/2012 | Welle | |
| 8,186,272 B2 | 5/2012 | Reichelsheimer et al. | |
| 8,211,035 B2 | 7/2012 | Melker et al. | |
| 8,219,327 B2 | 7/2012 | Nova et al. | |
| 8,223,964 B2 | 7/2012 | Stierman et al. | |
| 8,232,104 B1 | 7/2012 | Frazier | |
| 8,232,112 B2 | 7/2012 | Willson et al. | |
| 8,253,115 B1 | 8/2012 | Stevens et al. | |
| 8,293,948 B2 | 10/2012 | Chiba et al. | |
| 8,362,447 B2 | 1/2013 | Lambert | |
| 8,415,164 B2 | 4/2013 | Hayward et al. | |
| 8,415,165 B2 | 4/2013 | Liang et al. | |
| 8,426,216 B2 | 4/2013 | Kwok et al. | |
| 8,434,375 B1 | 5/2013 | Syage | |
| 8,470,605 B2 | 6/2013 | Putnam et al. | |
| 8,481,976 B1 | 7/2013 | Stevens et al. | |
| 8,491,225 B2 | 7/2013 | Valerino, Sr. | |
| 8,501,481 B1 | 8/2013 | Fraser | |
| 8,517,274 B2 | 8/2013 | Ciurczak et al. | |
| 8,561,486 B2 | 10/2013 | Novosselov et al. | |
| 8,562,853 B2 | 10/2013 | Leck et al. | |
| 8,623,822 B2 | 1/2014 | Arbogast et al. | |
| 8,624,215 B2 | 1/2014 | Hewak et al. | |
| 8,628,980 B2 | 1/2014 | Willson et al. | |
| 8,632,753 B2 | 1/2014 | Fan et al. | |
| 8,642,010 B2 | 2/2014 | Sato et al. | |
| 8,653,479 B2 | 2/2014 | Carroll et al. | |
| 8,663,603 B2 | 3/2014 | Arbogast et al. | |
| 8,668,873 B2 | 3/2014 | Almirall et al. | |
| 8,669,536 B2 | 3/2014 | Ma et al. | |
| 8,703,493 B2 | 4/2014 | Bronchetti et al. | |
| 8,716,027 B2 | 5/2014 | Bronchetti | |
| 8,732,570 B2 | 5/2014 | Gormish et al. | |
| 8,748,848 B1 | 6/2014 | Li et al. | |
| 8,781,197 B2 | 7/2014 | Wang et al. | |
| 8,857,278 B2 | 10/2014 | Syage | |
| 9,024,766 B2 | 5/2015 | Hood et al. | |
| 9,029,823 B2 | 5/2015 | Hewak et al. | |
| 9,046,453 B2 | 6/2015 | Calio et al. | |
| 9,056,138 B2 | 6/2015 | Fan et al. | |
| 9,057,712 B1 | 6/2015 | Fraser | |
| 9,073,091 B2 | 7/2015 | Cadieux, Jr. | |
| 9,075,020 B2 | 7/2015 | Lawandy | |
| 9,080,987 B2 | 7/2015 | Faenza | |
| 9,097,668 B2 | 8/2015 | Cadieux, Jr. | |
| 9,176,208 B2 | 11/2015 | Kalechofsky | |
| 9,189,604 B2 | 11/2015 | Lawandy | |
| 9,222,926 B1 | 12/2015 | Fraser | |
| 9,226,874 B2 | 1/2016 | Siegel | |
| 9,227,024 B2 | 1/2016 | Deutsch | |
| 9,233,049 B2 | 1/2016 | Siegel | |
| 9,239,327 B2 | 1/2016 | Natan et al. | |
| 9,243,169 B2 | 1/2016 | Lacoste et al. | |

(56) References Cited

U.S. PATENT DOCUMENTS

| | | |
|---|---|---|
| 9,244,017 B2 | 1/2016 | Cadieux, Jr. et al. |
| 10,086,938 B2 * | 10/2018 | Duesterhoft .............. B64D 1/02 |
| 2002/0000517 A1 * | 1/2002 | Corso .................... B01J 20/261 |
| | | 250/288 |
| 2002/0094058 A1 | 7/2002 | Kaiser et al. |
| 2002/0097832 A1 | 7/2002 | Kaiser et al. |
| 2002/0097833 A1 | 7/2002 | Kaiser et al. |
| 2002/0134933 A1 | 9/2002 | Jenkins et al. |
| 2003/0003394 A1 | 1/2003 | Lawandy et al. |
| 2003/0021941 A1 | 1/2003 | Lawandy |
| 2003/0058990 A1 | 3/2003 | Kaiser et al. |
| 2003/0134333 A1 | 7/2003 | Dehlinger et al. |
| 2003/0189167 A1 * | 10/2003 | Schultz .............. G01N 30/7266 |
| | | 250/281 |
| 2003/0194052 A1 | 10/2003 | Price et al. |
| 2003/0194053 A1 | 10/2003 | Schramm et al. |
| 2004/0022355 A1 | 2/2004 | Kaiser et al. |
| 2005/0008671 A1 * | 1/2005 | Van Antwerp ....... A61K 31/496 |
| | | 424/423 |
| 2005/0037181 A1 | 2/2005 | Lawandy |
| 2005/0058800 A1 | 3/2005 | Lawandy et al. |
| 2005/0183490 A1 * | 8/2005 | Grayfer ................. B01D 53/22 |
| | | 73/23.2 |
| 2005/0228268 A1 * | 10/2005 | Cole ..................... A61B 5/1112 |
| | | 600/420 |
| 2005/0252273 A1 * | 11/2005 | Imoto ...................... G01N 1/24 |
| | | 73/23.2 |
| 2006/0038979 A1 | 2/2006 | Natan et al. |
| 2006/0062734 A1 | 3/2006 | Melker et al. |
| 2006/0063271 A1 | 3/2006 | Putnam et al. |
| 2006/0086901 A1 | 4/2006 | Price et al. |
| 2006/0088946 A1 | 4/2006 | Willson et al. |
| 2006/0283931 A1 | 12/2006 | Polli et al. |
| 2007/0034024 A1 | 2/2007 | Syage |
| 2007/0158593 A1 | 7/2007 | Partin et al. |
| 2007/0165209 A1 | 7/2007 | Natan et al. |
| 2007/0181867 A1 | 8/2007 | Hewak et al. |
| 2007/0224128 A1 | 9/2007 | Dennis et al. |
| 2008/0041542 A1 | 2/2008 | Gray et al. |
| 2008/0059226 A1 | 3/2008 | Melker et al. |
| 2008/0156100 A1 * | 7/2008 | Hines .................... G01N 29/022 |
| | | 73/584 |
| 2008/0169926 A1 | 7/2008 | Reep |
| 2008/0293052 A1 | 11/2008 | Liang et al. |
| 2008/0299559 A1 | 12/2008 | Kwok et al. |
| 2009/0035533 A1 | 2/2009 | Starling et al. |
| 2009/0042191 A1 | 2/2009 | Hayward et al. |
| 2009/0084201 A1 | 4/2009 | Almirall et al. |
| 2009/0248319 A1 | 10/2009 | Call et al. |
| 2009/0255986 A1 | 10/2009 | Starling et al. |
| 2009/0275075 A1 | 11/2009 | Dodd et al. |
| 2009/0286250 A1 | 11/2009 | Hayward et al. |
| 2009/0309016 A1 | 12/2009 | Almirall et al. |
| 2010/0072278 A1 | 3/2010 | Putnam et al. |
| 2010/0089419 A1 * | 4/2010 | Field ..................... A45D 34/04 |
| | | 134/6 |
| 2010/0133150 A1 | 6/2010 | Chakrabarty et al. |
| 2010/0210009 A1 | 8/2010 | Willson et al. |
| 2010/0255603 A9 | 10/2010 | Putnam et al. |
| 2010/0258718 A1 | 10/2010 | Welle |
| 2010/0288943 A1 | 11/2010 | Lambert |
| 2010/0289655 A1 | 11/2010 | Elrod et al. |
| 2011/0036921 A1 * | 2/2011 | Hess ...................... A61L 9/01 |
| | | 239/44 |
| 2011/0050431 A1 | 3/2011 | Hood et al. |
| 2011/0070153 A1 | 3/2011 | Hyde et al. |
| 2011/0070154 A1 | 3/2011 | Hyde et al. |
| 2011/0092961 A1 | 4/2011 | Hyde et al. |
| 2011/0100091 A1 * | 5/2011 | Harrup ................. C08G 79/025 |
| | | 73/23.35 |
| 2011/0114744 A1 * | 5/2011 | Ricciardi .................. A61L 2/22 |
| | | 239/4 |
| 2011/0186436 A1 | 8/2011 | Novosselov et al. |
| 2011/0203931 A1 | 8/2011 | Novosselov et al. |
| 2011/0242531 A1 | 10/2011 | Natan |
| 2012/0034155 A1 | 2/2012 | Hyde et al. |
| 2012/0034156 A1 | 2/2012 | Hyde et al. |
| 2012/0034157 A1 | 2/2012 | Hyde et al. |
| 2012/0039796 A1 | 2/2012 | Markou |
| 2012/0057165 A1 | 3/2012 | Natan et al. |
| 2012/0114554 A1 | 5/2012 | Desimone et al. |
| 2012/0278002 A1 | 11/2012 | Call et al. |
| 2012/0286046 A1 | 11/2012 | Ciurczak et al. |
| 2012/0316497 A1 | 12/2012 | Deutsch |
| 2013/0034498 A1 | 2/2013 | Willson et al. |
| 2013/0079733 A1 * | 3/2013 | Burt ..................... B05B 7/0012 |
| | | 604/290 |
| 2013/0091963 A1 | 4/2013 | Syage |
| 2013/0190192 A1 | 7/2013 | Lowe |
| 2013/0206604 A1 * | 8/2013 | Lutz ...................... C02F 1/008 |
| | | 205/337 |
| 2013/0239704 A1 | 9/2013 | Syage |
| 2013/0327671 A1 | 12/2013 | Ciurczak et al. |
| 2014/0106357 A1 | 4/2014 | Berrada et al. |
| 2014/0133222 A1 | 5/2014 | Hewak et al. |
| 2014/0178640 A1 | 6/2014 | Jauzein et al. |
| 2014/0205749 A1 | 7/2014 | Chen et al. |
| 2014/0272097 A1 | 9/2014 | Jung et al. |
| 2014/0339298 A1 | 11/2014 | Lacoste et al. |
| 2014/0341983 A1 | 11/2014 | Dennis et al. |
| 2015/0014984 A1 | 1/2015 | Decoux et al. |
| 2015/0024423 A1 | 1/2015 | Natan |
| 2015/0092811 A1 | 4/2015 | Su |
| 2015/0107475 A1 | 4/2015 | Jung et al. |
| 2015/0219732 A1 | 8/2015 | Diamond et al. |
| 2015/0242736 A1 | 8/2015 | Glazer |
| 2015/0278757 A1 | 10/2015 | Walden |
| 2015/0279646 A1 | 10/2015 | Almirall et al. |
| 2015/0297776 A1 | 10/2015 | Conroy et al. |
| 2015/0297777 A1 | 10/2015 | Conroy et al. |
| 2015/0297778 A1 | 10/2015 | Conroy et al. |
| 2015/0297779 A1 | 10/2015 | Conroy et al. |
| 2015/0302713 A1 | 10/2015 | Berrada et al. |
| 2015/0344376 A1 | 12/2015 | Bowers et al. |
| 2015/0375149 A1 | 12/2015 | McLeod et al. |
| 2015/0376818 A1 | 12/2015 | McLeod et al. |
| 2015/0376819 A1 | 12/2015 | McLeod et al. |
| 2015/0377792 A1 | 12/2015 | Renfro et al. |
| 2015/0377841 A1 | 12/2015 | Gaynor et al. |
| 2015/0377854 A1 | 12/2015 | Gaynor et al. |
| 2015/0379312 A1 | 12/2015 | McLeod et al. |
| 2015/0379703 A1 | 12/2015 | McLeod et al. |
| 2015/0379903 A1 | 12/2015 | McLeod et al. |

\* cited by examiner

Taggant Capsules on Substrate
with Barrier Layer

Fig. 1A

Ruptures Capsules

Canister Containing PFT
Fig. 6

Canister Containing PFT
Fig. 7

METHODS OF DELIVERY OF ENCAPSULATED PERFLUOROCARBON TAGGANTS

CROSS REFERENCE TO RELATED APPLICATIONS

The present application is a Continuation of U.S. application Ser. No. 14/740,149, filed Jun. 15, 2015, now U.S. Pat. No. 9,610,597, issued Apr. 4, 2017, which is a Continuation of U.S. application Ser. No. 13/659,995, filed Oct. 25, 2012, now U.S. Pat. No. 9,057,712, issued Jun. 16, 2015, which claims benefit of priority from U.S. Provisional Patent Application No. 61/552,428, filed Oct. 27, 2011, each of which is expressly incorporated herein by reference in its entirety.

FIELD OF THE INVENTION

The present invention relates to tracers or taggants, and more particularly to gaseous tracers and taggants.

BACKGROUND OF THE INVENTION

The use of encapsulated perfluorocarbon taggants has been demonstrated for a variety of tag, track and locate (TTL) applications. TTL involves the marking of people, places and things of interest to military, intelligence community and law enforcement agencies with a covert material that can be subsequently followed, found or identified.

Perfluorocarbons are generally non-toxic, safe, volatile, non-reactive, compounds, which are environmentally benign, especially when released on limited quantities. The ambient background concentrations of the five perfluorocarbons routinely used as tracers (PFTs) are in the range of parts per $10^{15}$ of air. The PFTs, by virtue of their high vapor pressure, provide the unique ability to permeate closed doors and windows, containers and luggage. On the other hand, PFTs can be optically or physically detected, and are impervious to electronic interference and other problems inherent with other tagging technologies. Once a location reaches steady state, the actively emitting tagged item will provide vapor traces that are detectable in the vicinity of the item (even temporarily following removal of the tagged item). By extending the detectable life of the perfluorocarbon tag materials, PFTs have been previously known to provide a unique tool for law enforcement in numerous applications including marking and tracking of currency and other non-invasive inspection scenarios when seeking various items of contraband under surveillance.

PFT technology has already been developed and utilized in various applications including: (1) detection of leaks in underground storage tanks; (2) detection of leaks in high-pressure, oil-filled electric transmission lines; (3) atmospheric tracing and air pollution dispersion studies; (4) building ventilation studies; (5) detection of tagged explosives (blasting caps) in airline luggage; (6) detection of leaks in natural gas pipelines; and (7) currency tracking in cases of kidnappings. It has also been proposed for early warning fire detection systems.

U.S. Pat. Nos. 3,991,680 and 4,256,038, expressly incorporated herein by reference, relate to methods of detecting small bombs to provide security against terrorist activities which can cause the destruction of civil aircraft in flight or detonate explosives in places where large groups of people congregate. These methods involve the tagging of explosive materials such as blasting caps with a so-called "vapor taggant" which can be "sniffed" and detected by suitable equipment. The vapor taggant disclosed in U.S. Pat. No. 3,991,680 is sulfur hexafluoride ($SF_6$) absorbed in a fluoropolymer. The vapor taggant disclosed in U.S. Pat. No. 4,256,038 is includes one or a plurality of the following compositions: perfluorocycloalkanes such as perfluorodimethylcyclobutane (PDCB), perfuoromethylcyclohexane (PMCH), and perfluorodimethylcyclohexane (PDCH); perfluoroaromatics such as hexafluorobenzene (HFB), octafluorotoluene (OFT), decafluorobiphenyl (DFBP), decafluoroxylene (DFX), octafluoronaphthalene (OFN), and pentafluoropyridene (PFP), perfluoroalkanes such as perfluorohexane (PFH), perfluoropentane (PFPT), and perfluorooctane (PFO), and perefluorocycloalkenes such as decafluorocyclohexene (DFCH) and octafluorocyclopentene (OFCP). Examples of elastomers which are compatible with several of these taggants are copolymers of vinylidene fluoride and hexafluoropropylene. The following PFT compositions are also particularly useful as taggants: pf-methylcyclopentane (PMCP); pf-1,2-dimethylcyclohexane (o-PDCH[1]); pf-1,3-dimethylcyclohexane (m-PDCH[1]); pf-1,4-dimethylcyclohexane (p-PDCH[1]), pf-trimethylcyclohexanes (PTCH), perfluorodecalin (Octadecafluorodecahydonaphthalene, PFD, CAS 306-94-5), and perfluoro(methyl) decalin (PFMD, CAS 306-92-3). These compositions may be combined, as desired, to form a specific "cocktail"; i.e., a taggant that can be selectively detected and discriminated with respect to other taggants.

As used herein. PFT's are intended to refer to a class of chemical entities which have at least one —$CF_2$—$CF_2$— portion, or otherwise has an optical spectral characteristics corresponding to those resulting from the highly electronegative fluorine substituents, such that the compound is spectrographically distinguishable at very low concentrations, i.e., less than ppm level, and preferably less than ppb levels, from environmentally common substances. In some cases, a non-perfluorinated fluorocarbons may also be suitable for use, and to the extent that these have similar or advantageous remote detection characteristics, have low toxicity, good environmental stability (but perhaps less so than the perfluorocarbons, to reduce detrimental long-term environmental persistence and global warming potential), and appropriate volatility and dispersion in air, these may also be included with the scope of PFTs as encompassed herein.

Taggant use involves the detection of gaseous vapors (in minor tracer quantities) that are emitted over time. As there are a plurality of separate usable tracers in the PFT family, each with its own "fingerprint", the PFTs can be combined in a range of combinations and concentrations, yielding thousands of discrete "signatures". This allows discrimination between various compositions and enables the individual detection of multiple products, or the tracking of individually tagged products to provide exact identification and location.

The PFT technology is the most sensitive of all tracer technologies because the ambient background levels of the routinely used PFTs are extremely low (in the range of parts per quadrillion-ppq), and PFTs can be measured down to those levels.

It is the physical and chemical inertness of the PFTs that not only prevents their loss in the atmosphere, but also helps in their separation and analysis from less stable interfering compounds and makes them biologically inactive; and thus safe to use. Their limited industrial use not only results in low ambient background concentration, but also limits the possibility of numerous higher local concentrations that might confuse detection capability. John H. Heiser and Arthur J. Sedlacek, "Using LIDAR to Measure Perfluorocarbon Tracers for the Verification and Monitoring of Cap and Cover Systems", Brookhaven National Laboratory (2005), www.ecd.bnl.gov/pubs/BNL-75583-2006-JA.pdf, expressly incorporated herein by reference, teaches the use of LIDAR to detect PMCH, a perfluorocarbon.

Mason K Harrup, "Use of Custom Polyphosphazenes as Tunable Matrices for the Controlled Release of PFTs" (White Paper), expressly incorporated herein by reference, discloses a "tuned" polyphosphazene matrix, having a balance of perfluoronated pendant groups designed to hold the PFT tightly, providing slow release, and polar pendant groups designed to be incompatible with the PFT, providing fast release, to thereby control the observed PFT release rate.

U.S. Pat. No. 6,025,200, expressly incorporated herein by reference, relates to remote optical detection of PFTs. U.S. Pat. No. 6,214,624, expressly incorporated herein by reference discloses the use of PFTs to track hydrocarbon liquids. U.S. Pat. No. 5,409,839, expressly incorporated herein by reference, is entitled and describes a method for the tagging and detection of drugs, crops, chemical compounds and currency with perfluorocarbon tracers. U.S. Pat. No. 6,617,591, expressly incorporated herein by reference, relates to remote detect ion of explosives, for example, buried mines. See also, U.S. Pat. Nos. 4,256,038, 4,520,109, 5,173,298, 5,362,568, 5,585,112, 5,853,752, 6,071,495, 6,196,056, 7,641,809, 7,767,457, 7,985,590, and US 20110100091, each of which is expressly incorporated herein by reference.

DESCRIPTION OF THE INVENTION

According to one embodiment of the invention, a method is provided for using Perfluorocarbon Tracers to Identify Personnel (Friend or Foe) on the Battlefield, e.g., traditional or urban. For example, an encapsulation formula of Perfluorocarbon tracers can be impregnated into one or both of the layers of separable patch, which prior to separation, has a minimal rate of PFT release, and after separation, has a steady rate of release sufficient to allow remote detection. The patch, for example, may be a tear-away Velcro patch adapted to be affixed to soldiers in a war zone. To prevent possible friendly-fire incidents, troops would separate the layers of the patch, thereby initiating a controlled release of the PFT vapors. Other "friendly" troops on the field of battle, equipped with sensors for the PFT emissions, which may operate passively by detecting absorption or fluorescent emission from normal light sources, or actively by stimulating optical emissions and/or measuring specific absorption. At night, for example, illuminators tuned to the fluorescent wavelength of the Perfluorocarbon gases and specially designed, wavelength-matched vision devices would thus be able to literally "visible" as a cloud that might surround or emanate directly from the friendly troops. Likewise, an automated system could be provided to automatically block fire against friendly troops, bypassing the user's discretion, and perhaps acting with faster response and accuracy.

Alternately, a tag may be placed on personnel or objects, to assist in tracking them. For example, a patch, liquid, or powder, may be surreptitiously applied to an enemy vehicle, which could then be tracked to its destination. In this case, the tag may also be used to guide munitions, rather than inhibit them.

In a normal scenario, multiple taggant compositions and combinations may be employed, for various purposes. Thus, even if an enemy were to gain control over a set of tags, it would have to know the encoding, which could change periodically, in order to effectively use them as a false defense or offensive tool.

Likewise, the detector may be provided which requires authentication, such as biometric, token, security code, or the like, which would impede unauthorized use. This technique is especially useful where the PFTs themselves are dynamically encoded, and therefore without certain secret knowledge, the output of the detector would be difficult to interpret at any given time. For example, according to one embodiment, the PFTs release a time coded plume, which may alternately indicate friend, foe, or other identification. Likewise, release of dummy PFTs may be employed, to obscure particularly encoded releases, and thus requiring a sophisticated detector.

It is noted that a sophisticated adversary might seek to develop measures to track a reading device, and thus a passive (relying on ambient illumination) or remotely operable illuminator is preferred in such circumstances. Likewise, it is preferred that the reader incorporate at least one sophisticated and difficult to obtain critical technology, to impede unauthorized recreation.

It is also useful to provide an interrogator detection system, in the event that unauthorized devices are or become available, so that the badge wearers can take immediate action to avoid personal or other risk, when an unauthorized interrogator is detected. For example, authorized interrogators may produce a cryptographically encoded emission, the authenticity of which is determinable by an authentication device. Even in the event that an authentic device is diverted, the encoding may be device-specific, permitting individual detection and countermeasures to be employed, without requiring all authorized devices to be modified. For example, if an interrogator includes a laser illuminator, the laser itself, or an associated signal, may be individually modulated corresponding to an encoded signal. In the event of an unencoded, unauthorized, or deauthorized encoding in an illuminator suitable for detecting PFTs, users can immediately detect this illuminator when targeted by it, and take countermeasures, such as targeting the illuminator for destruction, and removing the PFT emitting devices from their person or vehicles. The detectors may also be protected by code or biometrics, to prevent their unauthorized use.

It is noted that since there are a number of usable compounds which are perfluorocarbons, or are closely related to perfluorocarbons, a large number of "recipes" are available. Therefore, it is preferred that the reader or interrogator permit individual detection of the various usable compounds, as well as distinguishing the components of a mixture and/or quantitatively determine ratios thereof. Typically, this detection will employ a laser illuminator to determine a specific spectrographic and/or fluorescence optical response of each PFT employed.

The reader or interrogator will typically employ a narrow bandwidth directional illumination source. The specific absorption wavelengths for perfluorocarbons and related compounds are in the UV range. Thus, a suitable illuminator would be a filtered broadband lamp, UV LED, LED (or other source) excited photon capture UV fluorescent emitter, a laser, or other emission source. Typically, a high efficiency design is preferred, since a low efficiency illuminator would emit heat and have high power demands, limiting portability and duration of battery life. Thus, a preferred design employs an LED excited emitter, or electroluminescent design, to provide a significant battery life and a low level of undesired emissions.

The detector is typically a spectrophotometric-type detector, capable of distinguishing specific PFT signatures from interfering emissions or absorptions. It is also preferably battery operated and small. The detector may also be provided as a broadband sensitive detector with one or more specific filters.

The PFT emitting device itself is, for example, a flat sheet-like patch, for example 1-25 square inches, composed of two sheets which are impermeable to perfluorocarbon vapors. These may be, for example, metallized or aluminized Mylar® Biaxially-oriented polyethylene terephthalate (boPET) polyester film, or other suitable material. A base sheet preferably has a removable attachment means, such as Velcro®, snaps, magnets, or other suitable method for removable attachment, e.g., to a uniform or object. Between the sheets is a controlled release perfluorocarbon material. For example, a polyphosphazine matrix, wax, or other material impregnated with PFT's, or microencapsulated PFT's in a matrix, is provided, which selectively adheres to the base sheet. The controlled release perfluorocarbon material is covered during storage with a cover sheet which is removable, and which easily releases from the controlled release perfluorocarbon material. For example, an adhesive or heat-generated seal is formed around the periphery junction of the two sheets, which is frangible when subjected to a peeling force.

While a relatively homogeneous material (i.e., homogeneous matrix or embedded microcapsule matrix) is preferred, a macroscopic barrier or atomizer may also be used to control release of PFT. In the later case, a pump, MEMS device, piezoelectric device, bubble jet, or other electrically operated device may be operated to release PFT. Such a device could have an electronic control, capable of arbitrary release profile generation, and remote activation/deactivation. Likewise, the device could employ separate control over a plurality of tracers, each with a separate release profile. Thus, an authorized device could have a predefined but secret temporal release profile (for example defined by a cryptographic function), allowing authentication of PFT releasing devices. The device could further have RF-ID attributes and/or a wireless receiver for remote controllability. Advantageously, an electronic embodiment employs a zinc air battery, activated by unsealing, and thus storage stable and activated along with the release of PFTs. Indeed, a film battery technology may permit formation of the battery together with the film forming the barrier to contain the PFT prior to intended release. Typically, a seal is provided for storage, since even low levels of unintended leakage over time will deplete the device and potentially pollute the atmosphere, making specific detection more difficult.

During storage, the sheets thus prevent release of PFT, while when the cover sheet is removed, the PFT is continually or controllably released over an extended period. It is preferred that, in a passive device, the release be at a relatively constant rate. Various known methods for temporally controlling release rates, such as employed in conjunction with pharmaceuticals, may also be employed. See, e.g., Temporal Control of Drug Delivery, Hrushesky, Langer, & Theeuwes, Eds., NY Acad. Sci 618 (1991), expressly incorporated herein by reference, and especially, Langer, Robert & Kost, Joseph, "Real Time Response Polymeric Delivery Systems", pp. 330-334.

Preferably, the PFT is not a single material, but at least two different materials, which are combined such that they are both released in detectable quantities. This combination permits coding of the patches, and makes counterfeiting more difficult. It likewise facilitates detection, since the composite spectral signature will have more features available for analysis. It is noted that, in the case of a combination release, it is possible to employ a different composition entirely, for example one that is not a PFT. Preferably, the detection system for the plural compositions will include substantial common elements, although this is not required.

Another aspect of the invention provides a method of using tracers to identify "friendly" vehicles, e.g., on the battlefield. For example, an encapsulated formulation, either in the form of a patch, or aerosolized by an aerosolizing apparatus, can used in conjunction with a vehicle, for example, tanks, HUMVEES, personnel carriers, Jeeps, etc. The vehicle will this emit a distinguishable plume, which can be remotely detected by its characteristic fluorescent pattern, can be used to identify various "friendly" vehicles. The detector can be used as part of a manual weapons targeting system, or as part of an automated trigger inhibition or fusing system.

On the other hand, such a plume may also be used to target or track vehicles (e.g., enemy or suspect) or other objects, especially where it is not the vehicle, but its future contents, which are of interest, since tagging the vehicle will generally require intimate contact.

A further aspect of the invention provides a method and composition for tracking, detecting and/or identifying suspected terrorists or criminals by ingestion, or for tracking potential kidnap or abduction risks. It has been determined that following exposure to perfluorocarbon materials that a human subject will emit a detectable chemical signal of perfluorocarbon for a period of up to one month, or longer depending upon individual metabolism and exposure dosage. The perfluorocarbons are emitted through bodily pores, excreted bodily fluids, and/or exhalation.

It is thus known that perfluorocarbons can be retained in the human body for extended periods of time. This is particularly obvious in the presence of technologies such as the DSITMS which provides very low detection levels in real-time. In the course of preparing for the demonstrations described below, it was noted that perfluorocarbon could be detected from one of the researchers at the Oak Ridge National Laboratory (breath, skin, urine) for three days after limited contact with a wax crayon formulation. Perfluorocarbons are nonmetabolizable, however, they do induce hepatic metabolizing enzymes. PFD given to rats was shown to induce cytochrome P-450 in a manner similar to phenobarbital. As with Phenobarbital induction, the activities of cytrochrome P-450 IIA1 and IIA2 (a.k.a. cytochrome P450$_b$ and cytochrome P450$_e$) were increased approximately two-fold following PFD treatment. Likewise, the activities of benzphetamine-N-demethylase and aldrin-epoxidase were increased. The activities of cytochrome P-450 IA1 and IA1 (induced by 3-methylcholanthrene-type inducers) and cytochrome P450 IV (induced by fatty acids and perfluorinated fatty acids) were unaffected. Although the perfluorocarbons are sequestered in the fat and later transferred to the liver, over time they are eliminated from the body via the lungs by exhalation. See, Final Report for CRADA Number ORNL99-0562, under funding from Tracer Detection Technology Corp. under contract of the National Institute of Justice, Jul. 26, 2000.

By incorporating encapsulated Perfluorocarbon tracers into food stuffs or other supplies or provisions anticipated to be delivered to, being transported to the hideouts of, or ingested by mammals of interest, the location, even if hidden, can be remotely detected. In this embodiment, preferably a pure form of PFT, or an encapsulation formulation thereof, in which the PFT can be mixed with food, other ingestible items or other supplies which are ultimately ingested, will emit a plume of the vapor taggant that can be detected through various means of sensing. Alternately, the PFT is released or volatilized during cooking, and thus the location of a "hideout" may be determined by searching for an associated plume from this release. Therefore, the PFT may be absorbed in, or placed in conjunction with, a food which requires cooking, such as rice.

The present invention further encompasses a method of using PFTs to track, detect and identify suspected terrorists or criminals, or hideouts of terrorists or criminals, by marking vehicles suspected of traveling to terrorist or criminal hideouts or other objects which are carried to these locations.

Effective inspection of large containers and trucks for controlled substances and narcotics is essential for the success of drug interdiction efforts. A significant fraction of drugs are smuggled through this avenue. Without prior knowledge provided through intelligence activities, the chances for drug detection are very slim. A successful drug interdiction program therefore requires efficient, rapid and cost-effective inspection techniques for large objects. The current technique used to thoroughly inspect containers is manual, highly labor intensive and can hardly be expanded to meet the challenge of abating the flow of illicit drugs from one country to another. Hence, an efficient way to meet the goal of an effective counter-drug effort is to provide a rapid, automatic, non-intrusive inspection system to inspect shipments and cargo containers without removing all of the contents for manual inspection. Thus, if a shipment can be tagged near its point of origin, it may be tracked using PFTs to distribution, permitting an entire chain to be tracked, without seizing the contraband at an intermediate stage.

In order for PFT tagging to function effectively, the release should be of sufficient concentration as to enable unambiguous identification, and also should be sufficiently long-lasting as to fulfill various usage parameters. Thus, in order to provide a sustained release of PFTs, a matrix is provided which provides a desired release profile. One type of matrix is a paraffin wax matrix or one based on large molecule inclusion complexes, however, such matrices may be difficult to control.

Polyphosphazenes are a class of polymers with backbones consisting of alternating phosphorus and nitrogen atoms. A repeating unit in polyphosphazenes is shown below, where the side groups G can be organic, inorganic or organometallic, and need not be the same. Interest in these polymers relies on the fact that, compared to various other biodegradable polymer materials, polyphosphazenes are easier to manipulate with different side groups. In addition, their physical and chemical properties are greatly affected by the nature of the side groups. Therefore, polymers with a wide range of properties can be obtained by appropriately choosing side chain groups. The possibility of obtaining polyorganophosphazene with different tunable properties makes those polymers potentially useful in many fields, ranging from pharmaceutical, industrial to agricultural applications. See, Shan Cheng, Stimuli-Responsive Polyphosphazenes as Controlled Drug Delivery Matrix Materials (2001), dspace.library.drexel.edu/retrieve/963/end.pdf.

Two different fundamental routes to synthesize substituted polyphosphazenes are generally used. A first method one starts from substitution reactions of the chlorine atoms on hexachlorocyclotriphosphazene to prepare phosphazene cyclic trimers with different side groups. By ring-opening polymerization of these small cyclic trimers, polyphosphazenes with different substituents can be obtained.

Many new materials have been prepared through this direct synthesis. However, the steric hindrance effect greatly limits the variety and the amount of the substituent on polymer chains. To solve this problem Allcock and his co-workers developed a synthesis route which involves the preparation of poly(dichlorophosphazene) and a sequential substitution reaction of chlorine atoms. In the first step, poly(dichlorophosphazene) as highly reactive macromolecular intermediate, can be prepared by several different methods. The most effective route to high molecular weight poly(dichlorophosphazene) is via the ring-opening polymerization of the cyclic trimer, hexachlorocyclotriphosphazene at 250° C. in the molten phase or in solution. This reaction gives a polymer with a broad molecular weight distribution, but with an Mw near 2,000,000, which corresponds to approximately 15,000 repeating units per chain. More recently, a room-temperature, living cationic condensation polymerization of Me3SiN=PCl3 method has also been developed. This reaction yields narrow molecular weight distribution polymers, with excellent control of the molecular weight and access to block copolymers.

The second step in the synthesis involves the replacement of the chlorine atoms by reactions with different organic or organometallic groups. Typically, an average of 30,000 chlorine atoms per molecule could be replaced at this stage as the result of high reactivity of the P—Cl bond. Based on this macromolecular substitution reaction, several hundred different polyorganophosphazenes have been synthesized. Most of the current industrial important polyphosphazenes are made by this method.

As a relatively new biodegradable polymer, polyphosphazene as drug delivery material has been widely studied. Compared with other drug delivery matrix materials, polyphosphazene shows particular advantages because it has an inorganic backbone that is biocompatible over time and that degrades to harmless small molecule products: ammonia, phosphate, and water. The system can be tailored to respond to different physiological environmental conditions by appropriate choice of substituted side chains. Many results show that the delivery systems designed with this material can accommodate a large variety of drugs including small drugs and macromolecules. Release study has been explored with both hydrophobic and hydrophilic polyphosphazene. The former ones are usually studied for polymer matrix erosion and diffusion release systems, while the latter ones are used to prepare hydrogel matrices after being cross-linked.

With respect to perfluorocarbons, it is well known that they have a high self-affinity, and this a fluorinated alkyl or perfluorinated substituent will be compatible with the PFT, thus leading to a high loading capacity and slowed release. Likewise, PFTs are incompatible with polar substituents, leading to lower loading capacity and higher release rates. As is known, the properties of a matrix may be tailored by balancing the proportions of the various substituents.

An alternate method for controlling release rate of PFTs is to provide a mechanical barrier, such as a perforated sheet, which allows volatilization dependent on the perforated area. In this case, the release rate is decoupled from the PFT holding capacity, though the mechanical structure is somewhat more complex and the composite structure will be more sensitive to mechanical treatment during use.

Figure 1A:
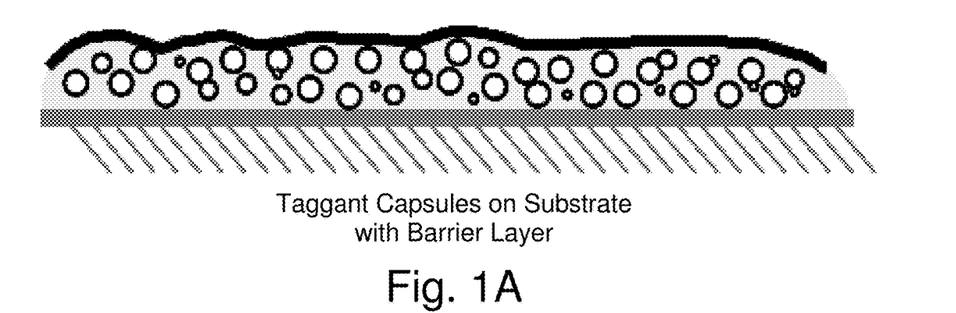
FIGS. 1A and 1B show representative cross sections of a tracer releasing apparatus having taggant capsules within a matrix, on a barrier layer, before and after release of the barrier.
Figure 1B:
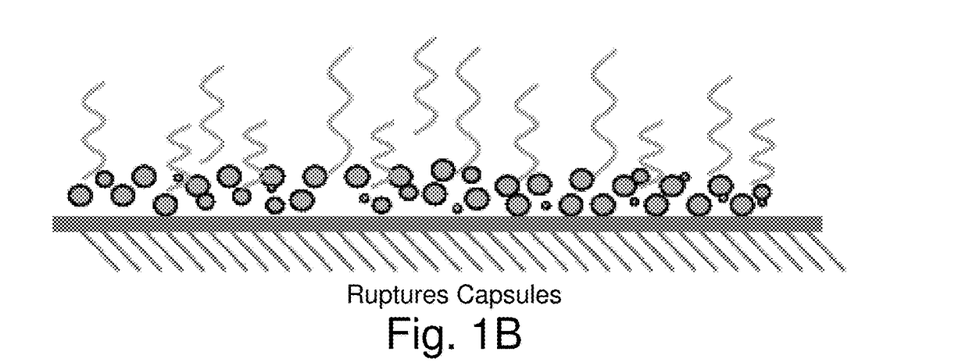

Indeed, both a matrix and a barrier technique may be combined, for example as shown in FIGS. 1A and 1B. FIG. 1 shows a representative cross section of a perfluorocarbon tracer having taggant microcapsules within a matrix, on a carrier layer, before and after release of a cover layer. The taggant capsules provide a relatively high bulk storage capacity, while the matrix provides release profile control. Typically, the matrix will be saturated with taggant, with the capsules providing a replenishing source. The release rate will be dependent on the surface area and an air-matrix release coefficient for the taggant, which in turn will be dependent on the vapor pressure of the taggant and the affinity of the matrix for the taggant.

The present invention therefore provides a system and method for identifying and tracking persons and objects, comprising use of a controlled taggant release device which has a very low rate of release prior to activation, and has an extended duration consistent rate of release after activation, which may be conveniently applied to persons or objects.

The present invention also provides a system for detection of taggant release device, comprising remote optical detection system which employs an illuminator emitting an optical wavelength for exciting a fluorescent emission from a taggant, and an imaging detector for sensing and/or imaging the excited fluorescence. This detector is preferably battery operated, portable by a human. The device may operate independently, but is preferably integrated with a fusing or triggering mechanism for munitions. The device is further preferably configured as part of an "identify friend or foe" (IFF) system, which may be manually or automatically operable. In one embodiment, the detector or imager is mounted on an unmanned vehicle, such as an unmanned aerial vehicle (UAV).

It is therefore an object of the invention to provide a method of using volatile perfluorocarbons to identify personnel, comprising the steps of applying a selectively activatable controlled release perfluorocarbon to a person. Preferably, the controlled release mechanism employs a substituted polyphosphazene matrix. The PFT is preferably one or more perfluorocarbons selected from the group of PMCH, PMCP, o-PDCH', m-PDCH', p-PDCH' and PTCH. The controlled release is preferably initiated by removal of a barrier, such as a confining film. Preferably, the controlled release continues after initiation for 4-48 hours, and thereafter occurs at only a low level. Longer duration formulations may also be provided. The PFT matrix may be provided as an aerosol, paint or powder. The PFT is preferably released from a substituted polyphosphazene matrix, formulated to control a capacity and release profile of the PFT from the matrix.

The volatile perfluorocarbons may also be used to identify land vehicles. Thus, according to another embodiment, it is an object of the invention to provide a method of using perfluorocarbon tracers to identify vehicles, comprising of the steps of applying a formulation of perfluorocarbon tracers in a paint or aerosol spray to a vehicle, and detecting the vehicle remotely based on perfluorocarbon emissions.

According to a further embodiment of the invention, a PFT is provided as a part of a food or liquid product, for human ingestion. Preferably, the PFT is provided in a PFT-polyphosphazene matrix, in such form as it will not release until heated or otherwise changed chemically. The PFT can be detected by urinalysis, breath testing, of other body fluid testing. Vapor emissions may be used to detect the location of a tagged individual.

Some ways of providing taggant include micro-encapsulated granules containing Perfluorocarbon as well as other forms in which a packet (like an envelope) is provided.

The present invention provides new methods of delivery of encapsulated Perfluorocarbon taggants, which might be used on the field of battle by the military or agencies of the Intelligence community, as well as materials to be used by certain law enforcement agencies.

These applications may include but are not limited to:

(1) Projectiles

Various projectile designs are provided:

Frangible projectiles in which an encapsulated form of Perfluorocarbon are combined with the explosive materials such as black powder; these projectiles are designed to maintain ballistic integrity but are also destroyed without leaving a residue upon impact. These materials may include but not be limited to natural or synthetic clay, polymers, or combinations of clays and polymers capable of limiting or fully preventing permeation of the encapsulated Perfluorocarbon from escaping until impact in a jacket provided by munitions manufacturers.

Projectiles containing a taggant consisting of a starch-like material like beta-Cyclodextrin that can "hold" the Perfluorocarbon within it prior to impact but that are released by the force of the impact and physical macroscopic disintegration of the carrier at the target sight.

Projectiles containing a taggant consisting of an encapsulated Perfluorocarbon in a sponge or other absorbent material (absorbent clay or synthetic material) that can contain a liquid Perfluorocarbon such that the vapors do not escape until the taggant munition strikes the intended target.

The absorbent material may contain a substance that attenuates the dissipation of the PFT from the carrying material.

The absorbent material may contain a substance that both attenuates the dissipation of the PFT from the carrying material and also leaves a residue on the target that persists. The residue may be a continuing emitting Perfluorocarbon taggant or may be a film that can be optically detectable. The optical detection of the residue may be detectable from a distance with a specially tuned vision system and light source specific to the absorption band of the residue material, or in close proximity by shining a light on the residue surface and seen in the visible light range.

This projectile form of taggant can be launched from a distance by artillery, applied by a "sponge-like" carrier by manually imparting the sponge at a surface, brushed onto a surface or sprayed.

The projectile may contain a combination of granular materials and softeners that splatter on impact on the target surface.

(2) Sprays

Figure 2:
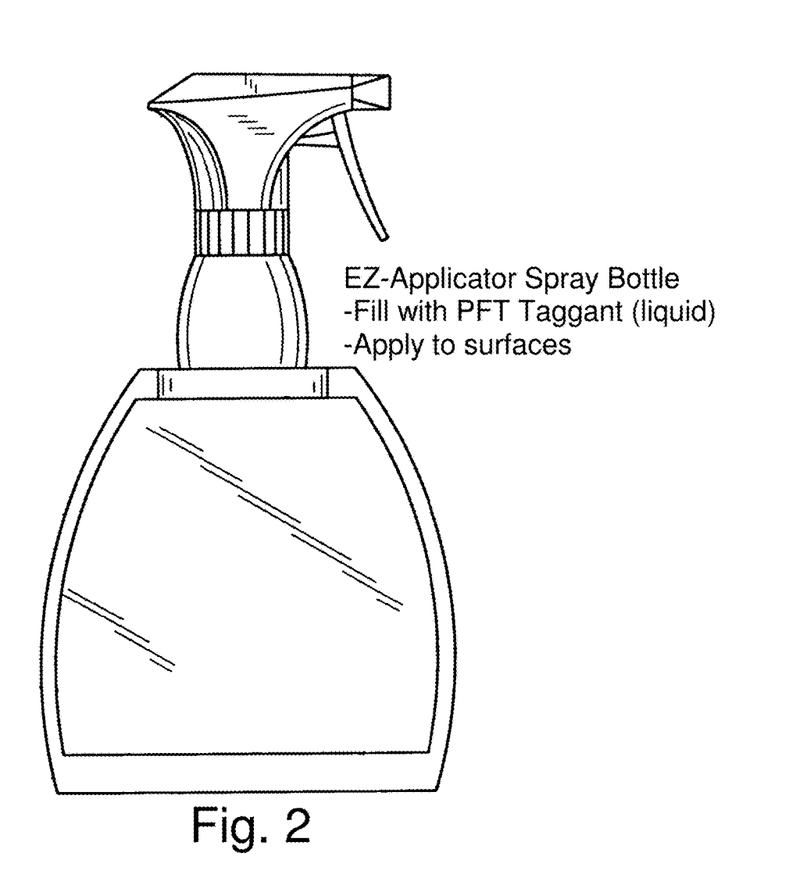
FIGS. 2-9 show various embodiments for control of release of tracer compositions.
Figure 3:
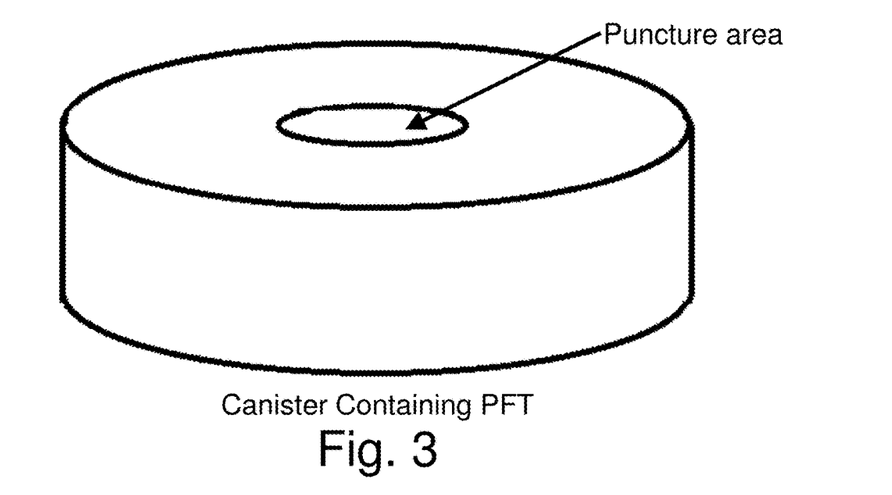
Figure 4:
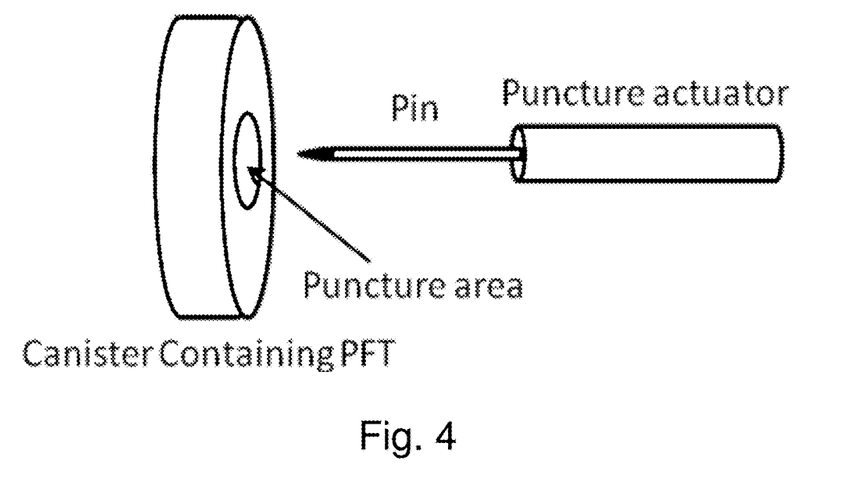
Figure 5:
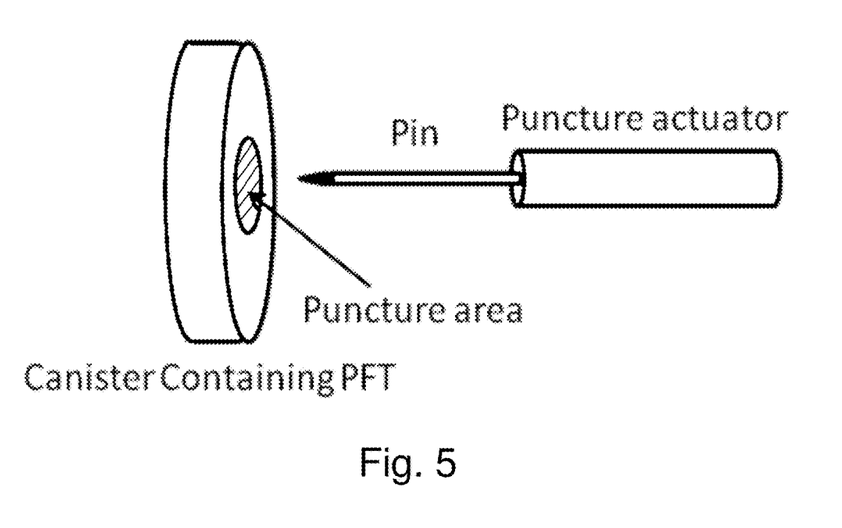
Figure 6:
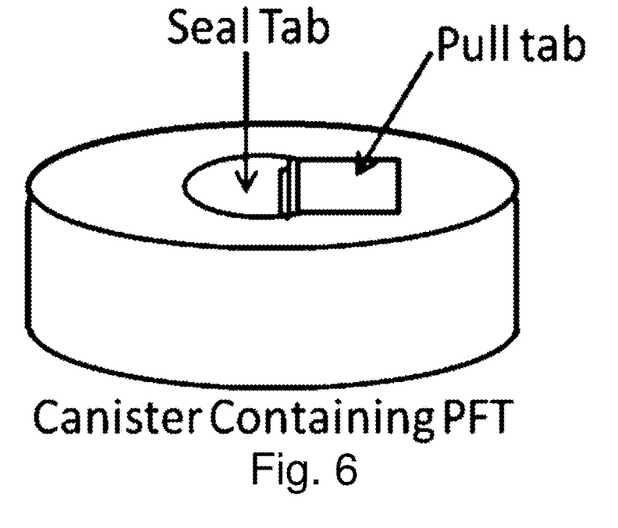
Figure 7:
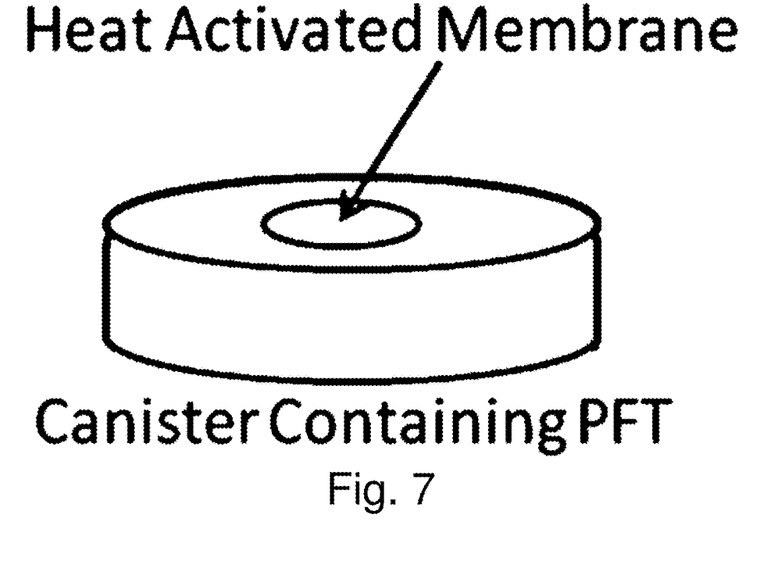
Figure 8:
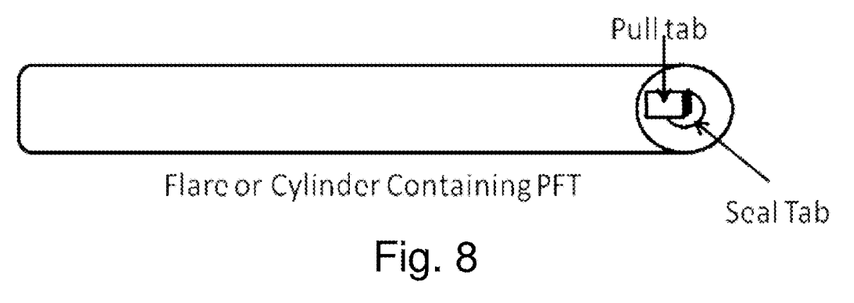

Spraying can be accomplished through an applicator (aerosol and non-aerosol) or by methods similar to crop dusting of pesticides from an airplane or from higher altitudes by unmanned air vehicles (UAV). See, FIG. 2.

In the preferred embodiment, the Perfluorocarbon would be contained in minute particles imperceptible to the naked eye and yet containing sufficient PFT in the aggregate such that when the water or other carrying liquid evaporated, a deposit of taggant would remain on the surface.

(3) Containers

Various container designs are provided:

Containers in which a reservoir of Perfluorocarbon is contained in a vacuum sealed container.

Containers containing a taggant consisting of an encapsulated Perfluorocarbon in a sponge or other absorbent material (absorbent clay or synthetic material) that can contain the liquid Perfluorocarbon such that the vapors do not escape until the container is punctured or opened in manners described below.

Containers configured in such a way that a rubber or permeable membrane is provided beneath the top surface of one of the surfaces of the container such that when the container is activated, that the Perfluorocarbon vapors "leak" or permeate through the permeable or other material membrane. See FIG. 3.

Containers in which the vacuum seal can be punctured manually to allow the release of a Perfluorocarbon taggant on activation.

Containers in which the vacuum seal can be punctured remotely to allow the release of a Perfluorocarbon taggant on activation. The remote activation can be accomplished by a pin actuator in a compartment containing a PFT canister with a puncture area and a mechanism that can be remotely activated (by cell phone of other radio signal) to punch a hole in the puncture area. Upon puncturing the puncture area, the Perfluorocarbon vapors are released over time through the permeable membrane. See FIG. 4.

This configuration can be secreted in a hidden compartment in a vehicle, piece of luggage or other conveyance to prevent illicit discovery of the taggants materials. This would be used for covert tagging, tracking and locating/identification of suspects in transit.

Containers that are pre-punctured but sealed with a material to prevent permeation of the Perfluorocarbon from the container (such as a Mylar label or other permanent seal material). The opening of this configuration would be the same as described directly above. See FIG. 5.

Containers can be opened in a variety of manners including but not limited to the user pulling on a "ring" that peals away from one of the flat surfaces of the container from the rest of the container. See. FIG. 6.

Canisters can also be configured to be able to be inserted covertly into enclosed areas that will upon activation release the Perfluorocarbon vapors. Envisioned are certain law enforcement and other covert surveillance applications in which a canister can be placed inside the exhaust pipe of a vehicle in such a way so as to not totally block the flow of air from the engine. However, based on the heat reactivity of the permeable membrane (or other membrane material), the Perfluorocarbon vapors would be emitted and expelled from the exhaust pipe, thus enabling agents to follow a tagged vehicle. See FIG. 7.

Alternatively, the exposed portion of the canister can be over-painted with a material like Glyptal (an insulating paint—see Dietz U.S. Pat. No. 5,362,568, expressly incorporated herein by reference), non-permeable resins or polymers or other blocking agents that degrade as temperature of the air flow increases.

(4) Signals or Flares

Various signal or flare designs are provided:

Containers in which a reservoir of Perfluorocarbon in contained in a vacuum sealed container.

Containers containing a taggant consisting of an encapsulated Perfluorocarbon in a sponge or other absorbent material (absorbent clay or synthetic material) that can contain the liquid Perfluorocarbon such that the vapors do not escape until the container is punctured or opened in manners described below. The preferred embodiment of a PFT signal flare would be a pull tab configuration as described in the canister embodiment. See FIG. 8.

When in a situation of danger, the user (lost soldier, downed pilot, lost or injured skier) would pull the tab on the canister and begin the slow and controlled release of Perfluorocarbon vapors to enable searchers or rescuers to locate and identify the individual. Cylinders could be made for varying lengths of duration.

(5) Impregnated Fibers and Fabrics

Fibers or fabrics that have been impregnated with an encapsulated form of Perfluorocarbon such that the vapor will emit upon activation. Using synthetic fibers and a combination of PFT compatible polymers, fibers can be coated during the coloration or dying process or the cloth materials can be coated during the finishing process with a material that will contain stable, non-emitting Perfluorocarbon. In this embodiment, the PFT vapors would be released upon exposure to sun light (or other specified wavelengths of light). This will occur through the use of matched polymers to the PFTs and which react to sun exposure.

Alternatively, release of the Perfluorocarbon vapors can occur when the fibers or fabric is exposed to a specific, predetermined wavelength of sound. A further embodiment of impregnated fibers or fabrics could also be upon exposure of the materials to other chemicals that are found in an ambient environment such as off gases of methamphetamine, cocaine or other illicit drug manufacturing.

(6) Shampoos, Soaps and Creams

Using a granular form of encapsulated Perfluorocarbon, the taggants can be incorporated in products like shampoos, soaps and creams. The granular PFTs would be combined with attenuators and coated in such a manner as to remain non-emitting so long as the capsules are not agitated or exposed to friction. This form of PFT delivery can also be used in hand lotions, liniments, pain rubs, and sanitizing liquids. The tiny granules will be imperceptible to the subject being "tagged" in this manner, but because of the nature of the extended release and tendency of the PFT to be absorbed through pores, the subject would be detectable long term using specific detectors or forensically through blood tests or urinalysis.

(7) Ingestible Forms

There are a number of ingestible forms of Perfluorocarbon taggants that can be used in tag, track and locate applications. In the form of a gel capsule, liquid PFT can be substituted for more common ingredients such as fish oil. The nature of Perfluorocarbon is that once in the body it will isolate in the liver and then be effused through the pores. This will enable forensic detection and confirmation of a target's identity.

By using a macromolecular form of encapsulated Perfluorocarbon with inclusion complexes like beta-Cyclodextrin which is a starch-like material, a PFT taggant can be disguised as normal food stuffs like rice or potatoes and will activate upon cooking. The released PFT vapor will be detectable by PFT specific detectors for a period of time and at distances separated from the source. Ideally, the detection will be accomplished through a specially tuned optical detection platform.

(8) Applicators (Mister)

Figure 9:
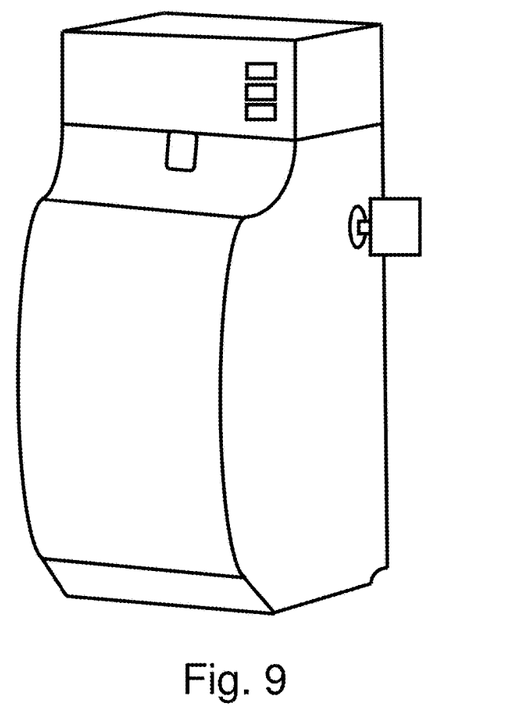

An applicator in which a measured amount of encapsulated Perfluorocarbon tracer is included and which in set time periods or on command will emit an amount of taggant to the area; alternatively, provide for a radio activated/radio controlled release of Perfluorocarbon taggant from the applicator to enable periodic releases thus leaving a trail of "puffs." See FIG. 9.

An applicator in a heat resistant package could be attached to the under carriage of a vehicle and upon activation, either through the heat generated by the vehicle or through a radio activation, will emit periodic "puffs" of chemical taggant.

Figure 10:
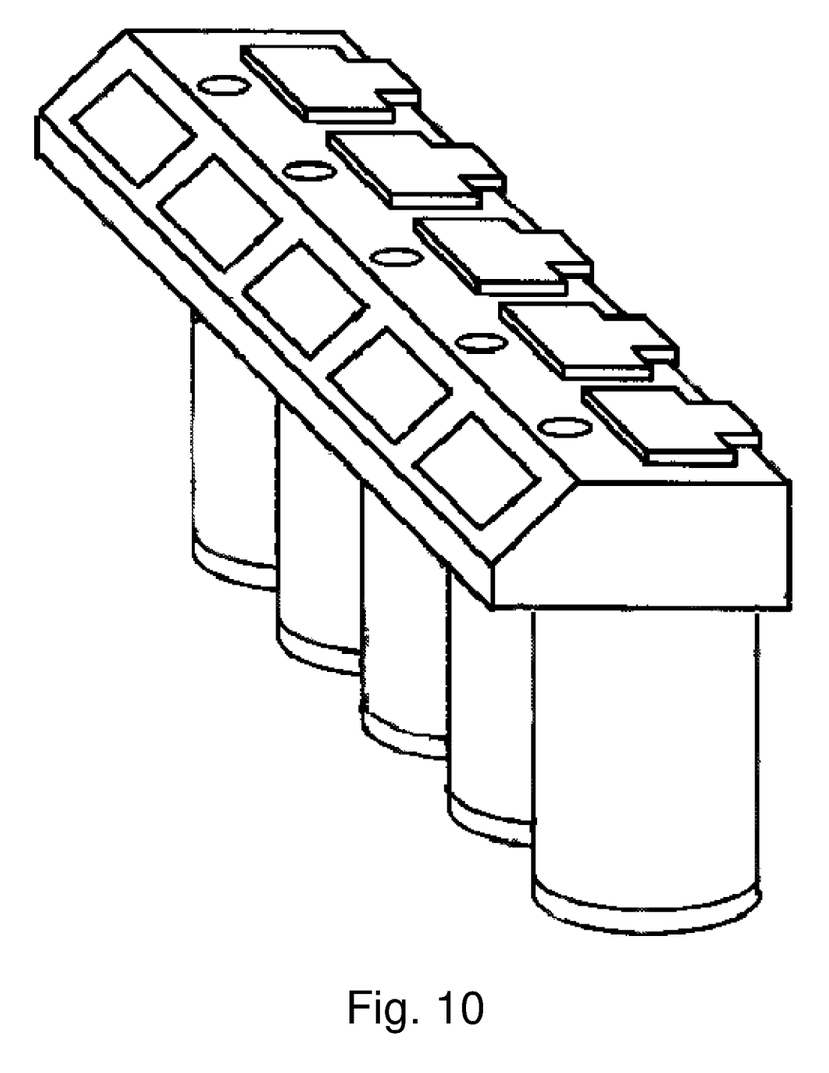
FIG. 10 shows an embodiment for electronically controlling release of a plurality of tracer compositions from a plurality of different reservoirs.

As shown in FIG. 10, a pump, MEMS device, piezoelectric device, bubble jet, or other electrically operated device may be operated to release PFT from a plurality of different reservoirs, each containing a respective volatile liquid. An electronic control, capable of arbitrary release profile generation, and remote activation/deactivation for each respective reservoir, is provided, which may be responsive to a wireless remote control. The device permits separate and independent control over a plurality of tracers, each with a separate release profile.

(9) Applicators (Droplets)

Using a low vapor pressure Perfluorocarbon, include this Perfluorocarbon in an applicator which when heated, will deposit the heat activated droplets of Perfluorocarbon, leaving a trail of liquid that will over time volatilize and create a traceable vapor.

(10) Taggant Additives

To enable canine tracking of a tagged individual or vehicle, modify the Perfluorocarbon molecule (append) an odorant which is imperceptible to humans but which enhance the ability for canine detection.

To enhance stand-off detection of the Perfluorocarbon, modify the molecule with a fluorescent marker to facilitate optical detection and to distinguish potentially interfering perfluorocarbon molecules and/or to distinguish tracers having different fluorescent signatures.

The numerous modifications and variations of the present invention are possible in light of the above teachings. It is therefore understood that within the scope of the appended claims, the invention may be practiced otherwise than as specifically described herein.

What is claimed is:

1. A device for emitting volatile fluid vapors into an environment, comprising:
    a power supply;
    a plurality of reservoirs, each being configured to contain a respective volatile fluid, configured to contain a respective volatile fluid except when dispensed;
    an electronic dispenser, configured to dispense the respective volatile fluid from the respective reservoir into the environment, in response to a respective electrical control signal, each electronic dispenser comprising at least one volatile fluid control device, selected from the group consisting of a microelectromechanical system (MEMS), a piezoelectric device, a bubble jet device, and a pump; and
    an electronic control, powered by the power supply, configured to generate the respective electronic control signals selectively in dependence on at least a received wireless remote control signal, to selectively and independently activate and deactivate the at least one volatile fluid control device for each respective reservoir, to thereby permit respectively different temporal dispensing profiles.

2. The device according to claim 1, wherein the at least one volatile fluid control device comprises a microelectromechanical system (MEMS).

3. The device according to claim 1, wherein the at least one volatile fluid control device comprises a piezoelectric device.

4. The device according to claim 1, wherein the at least one volatile fluid control device comprises a bubble jet device.

5. The device according to claim 1, wherein the at least one volatile fluid control device comprises a pump.

6. The device according to claim 1, wherein the at least one volatile fluid control device is configured to respond to an arbitrary release profile to dispense an amount of the respective volatile fluid over time corresponding to the arbitrary release profile.

7. The device according to claim 1, wherein the received wireless remote control signal comprises a radio frequency signal.

8. The device according to claim 1, wherein the received wireless remote control signal is generated by a cellphone.

9. A method for emitting volatile fluid vapors into an environment, comprising:
    providing dispensing device comprising:
        a power supply;
        a plurality of respective reservoirs for respective volatile fluids, each being configured to contain the respective volatile fluid except when dispensed;
        an electronic dispenser, configured to dispense the respective volatile fluid from each respective reservoir into the environment, in response to an electrical control signal, comprising a plurality of volatile fluid control devices, each being selected from the group consisting of a microelectromechanical system (MEMS), a piezoelectric device, a bubble jet device, and a pump; and
        an electronic control, powered by the power supply, configured to generate the electronic control signal selectively in dependence on at least a received wireless remote control signal, to selectively and independently activate and deactivate the plurality of volatile fluid control devices of the electronic dispenser, to thereby permit respectively different temporal dispensing profiles;
    receiving the wireless remote control signal;
    selectively activating the plurality of volatile fluid control devices in dependence on the received wireless remote control signal; and
    selectively deactivating the plurality of volatile fluid control devices in dependence on the received wireless remote control signal.

10. The method according to claim 9, further comprising sensing a vapor corresponding to a respective volatile fluid in the environment.

11. The method according to claim 9, wherein the plurality of volatile fluid control devices comprise a microelectromechanical system (MEMS).

12. The method according to claim 9, wherein the plurality of volatile fluid control devices comprise a piezoelectric device.

13. The method according to claim 9, wherein the plurality of volatile fluid control devices comprise a bubble jet device.

14. The method according to claim 9, further comprising pumping a respective volatile fluid from a respective reservoir.

15. The method according to claim 9, wherein the the plurality of volatile fluid control devices are each configured to respond to an arbitrary respective release profile to dispense an amount of a respective volatile fluid over time corresponding to the arbitrary respective release profile, further comprising:
generating the electronic control signal corresponding to the arbitrary respective release profile; and
dispensing an amount of the respective volatile fluid over time corresponding to the arbitrary respective release profile.

16. The method according to claim 9, further comprising receiving the wireless remote control signal as a radio frequency signal.

17. The method according to claim 9, wherein the received wireless remote control signal is generated by a cellphone.

18. A device for dispensing volatile fluids, comprising:
a plurality of reservoirs for a plurality of respective volatile fluids, each having a barrier wall configured to contain the respective volatile fluid, and a port configured to extract the respective volatile fluid from the reservoir;
an electronic dispenser, configured to dispense each respective volatile fluid received from the respective port as a respective puff into the environment, in response to an electrical control signal, comprising a mechanical spray device for each respective port; and
an electronic control, powered by the power supply, configured to generate the electronic control signal selectively and independently in dependence on at least a received wireless remote control signal, to generate respective puffs of respective volatile fluids from the respective mechanical spray devices, to thereby permit respectively different temporal dispensing profiles.

19. The method according to claim 18, wherein the electronic dispenser comprises at least one of a microelectromechanical (MEMS) device, a bubble jet device, and a piezoelectric device, and the wireless remote control signal is received through a wireless radio frequency communication from a cellphone.

20. The method according to claim 18, wherein the mechanical spray devices are configured to respond to an arbitrary respective release profile for each respective volatile fluid, and to dispense an amount of the respective volatile fluid over time corresponding to the arbitrary respective release profile.

21. The method according to claim 18, further comprising sensing the environment, and further controlling the electronic signal in dependence on the sensed environment.

* * * * *